United States Patent [19]

Kurjan et al.

[11] Patent Number: 4,546,082

[45] Date of Patent: Oct. 8, 1985

[54] E. COLI/SACCHAROMYCES CEREVISIAE PLASMID CLONING VECTOR CONTAINING THE ALPHA-FACTOR GENE FOR SECRETION AND PROCESSING OF HYBRID PROTEINS

[75] Inventors: Janet Kurjan, San Francisco; Ira Herskowitz, Berkeley, both of Calif.

[73] Assignee: Regents of the Univ. of California, Berkeley, Calif.

[21] Appl. No.: 389,560

[22] Filed: Jun. 17, 1982

[51] Int. Cl.[4] .................... C12N 15/00; C12N 1/16; C12N 1/18; C12N 1/00; C12P 21/00; C12P 21/02; C12P 21/04; C12P 19/34; C07H 21/02

[52] U.S. Cl. ........................... 435/172.3; 435/68; 435/70; 435/71; 435/91; 435/255; 435/256; 435/317; 536/27; 935/11; 935/28; 935/69; 935/79

[58] Field of Search .................. 435/68, 70, 91, 172, 435/255, 256, 317, 71, 172.3; 536/27

[56] References Cited

U.S. PATENT DOCUMENTS 4,338,397  7/1982  Gilbert et al. .................... 435/70

OTHER PUBLICATIONS

Sherman et al.: Methods in Yeast Genetics, Cold Spring Harbor Laboratory, 1982, p. 108A.
Herskovitz et al.: in *The Molecular Biology of the Yeast Saccharomyces*, Strathern et al. (ed), Cold Spring Harbor, 1981, pp. 182–184.
Astell et al.: Cell 27, 15, (1981).
Nasmyth et al.: Cell 19, 753, (1980).
Botstein et al.: Recombinant DNA Technical Bulletin 2(2), 49, (1979).
Thorner: in *The Molecular Biology of the Yeast Saccharomyces*, Strathern et al. (ed.), Cold Spring Harbor Laboratory, 1981, pp. 161–163.
Kurjan et al.: Cell 30, 933, (1982).
*Methods in Molecular Biology*, vol. 9, R. B. Wickner, Chap. 3, "Restriction Endonuclease from Hemophilus Influenzae RD", H. Smith, pp. 71–85, (1974).
*Methods in Molecular Biology*, vol. 9, R. B. Wickner, Chap. 4, "The EcoRI Restriction Endonuclease", P. J. Greene, et al., pp. 87–111, (1974).
*Methods in Molecular Biology*, vol. 9, R. B. Wickner, Chap. 5, "Restriction Endonucleases AP, GA, and H-I From Three Haemophilus Strains, Takanami, pp. 113–133, (1974).
*Science*, vol. 168, "Saccharomyces cerevisiae: A Diffusible Sex Factor", Duntze, et al., pp. 1472–1473, (Jun. 1970).
*Proc. of the Nat. Acad. of Sci.*, vol. 65, No. 2, "Selective Elimination of the Exonuclease Activity of the Deoxyribonucleic Acid Polymerase from *Escherichia coli* B by Limited Proteolysis", Klenow, et al., pp. 168–175, (Jan. 1970).
*J. of Bacteriology*, vol. 119, No. 2, "Mechanism of α Factor Biosynthesis in *Saccharomyces cerevisiae*", Scherer, et al., pp. 386–393, (Aug. 1974).
*Cell*, vol. 21, "Replication and Recombination Functions Associated with the Yeast Plasmid, 2μ Circle", Broach, et al., pp. 501–508, (Sep. 1980).
*Cell*, vol. 16, "Sequence of the Gene for Iso-1-Cytochrome c in *Saccharomyces cerevisiae*", Smith, et al., pp. 753–761, (Apr. 1979).
*Gene*, 8, "Transformation in Yeast: Development of a Hybrid Cloning Vector and Isolation of the CAN1 Gene", Broach, et al., pp. 121–133, (1979), by Elsevier/No. Holland Biomedical Press.

(List continued on next page.)

Primary Examiner—Thomas G. Wiseman
Assistant Examiner—James Martinell
Attorney, Agent, or Firm—Flehr, Hohbach, Test, Albritton & Herbert

[57] ABSTRACT

A method for producing secretable and processable biologically useful polypeptides in yeast is provided utilizing vectors including at least a segment of the gene coding for *S. cerevisiae* alpha-factor.

10 Claims, 6 Drawing Figures

OTHER PUBLICATIONS

*J. Mol. Biol.*, CXII, "Total Synthesis of the Structural Gene for an Alanine Transfer RNA from Yeast. Enzymic Joining of the Chemically Synthesized Polydeoxynucleotides to Form the DNA Duplex Representing Nucleotide Sequence 1 to 20", Sgaramella, et al., pp. 427-444, (1972).

*Methods in Enzymology*, vol. 65, "Sequencing End-Labeled DNA with Base-Specific Chemical Cleavages", Maxam, et al., pp. 499-560, (1977).

*Proc. Nat. Acad. Sci. USA*, vol. 69, "Curing of a Killer Factor in *Saccharomyces cerevisiae*", Fink, et al., pp. 2846-2849, (Oct. 1972).

*Proc. Nat. Acad. Sci. USA*, vol. 74, No. 2, "A New Method for Sequencing DNA", Maxam, et al., pp. 560-564, (Feb. 1977).

*Nature*, vol. 275, "Transformation of Yeast by a Replicating Hybrid Plasmid", Beggs, pp. 104-109, (Sep. 1978).

*Proc. Nat. Acad. Sci. USA*, vol. 79, "Partial Characterization of the mRNA that Codes for Enkephalins in Bovine Adrenal Medulla and Human Pheochromocytoma", Comb, et al., pp. 360-364, (Jan. 1982).

*Proc. Nat. Acad. Sci. USA*, vol. 75, No. 4, "Transformation of Yeast", Hinnen, et al., pp. 1929-1933, (Apr. 1978).

*Proc. Natl. Acad. Sci. USA*, vol. 77, No. 4, "Isolation of Genes by Complementation in Yeast: Molecular Cloning of a Cell-Cycle Gene", Nasmyth, et al., pp. 2119-2123, (Apr. 1980).

*Proc. Nat. Acad. Sci. USA*, vol. 69, No. 11, "Cleavage of DNA by $R_I$ Restriction Endonuclease Generates Cohesive Ends", Mertz, et al., pp. 3370-3374, (Nov. 1972).

*Proc. Nat. Acad. Sci. USA*, vol. 77, No. 10, "Nucleotide Sequence of a Cloned Structural Gene Coding for a Precursor of Pancreatic Somatostatin", Goodman, et al., pp. 5869-5873, (Oct. 1980).

*Nature*, vol. 278, "Nucleotide Sequence of Cloned cDNA for Bovine Corticotropin-B-lipotropin Precursor", Nakanishi, et al., pp. 423-427, (Mar. 1979).

*Genetics*, 83, "Interconversion of Yeast Mating Types-1. Direct Observations of the Action of the Homothallism (HO) Gene", Hicks, et al., pp. 245-258, (Jun. 1976).

*Molecular and Cellular Biology*, vol. 2, No. 1, "Isolation and Genetic Analysis of *Saccharomyces cerevisiae* Mutants Supersensitive to G1 Arrest by *a* Factor and α Factor", Chan, et al., pp. 11-20, (Jan. 1982).

*Proc. Nat. Acad. Sci. USA*, vol. 76, No. 10, "Control of Yeast Cell Types by Mobile Genes: A Test", Kushner, et al., pp. 5264-5268, (Oct. 1979).

*J. Mol. Biol.*, vol. 98, "Detection of Specific Sequences Among DNA Fragments Separated by Gel Electrophoresis", Southern, pp. 503-517, (1975).

J. Thorner, "Pheromonal Regulation of Development in *S. cerevisiae*", *The Molecular Biology of the Yeast Saccharomyces: Life Cycle and Inheritance*, (Strathern, et al., eds.), pp. 143-180, (1981).

Botstein, et al., "Principles and Practice of Recombinant DNA Research With Yeast", *The Molecular Biology of the Yeast Saccharomyces: Metabolism and Gene Expression*, (Strathern, et al., eds.), pp. 607-636, (1982).

Kurjan, et al., "A Putative Alpha-Factor Precursor Containing Four Tandem Repeats of Mature Alpha-Factor", Abstract accompanying oral presentation given Aug. 11-16, 1981 at Cold Spring Harbor, New York, Meeting on The Molecular Biology of Yeast., p. 242.

```
                                                                                    -170
                                                                                    AGTG
CAAGAAAAACCAAAAAGCAACAACAGGTTTTGGATAAGTACATATATAAGAGGGCCTTTTGTTCCCATCAAAAATGTTACTGTT
CTTACGATTCATTACGATTCAAGAATAGTTCAAACAAGAAGATTACAAACTATCAATTTCATACACAATATAAACGACCAAA pstI                                           50
AGA ATG AGA ATT CCT TCA ATT TTT ACT GCA GTT TTA TTC GCA GCA TCC TCC GCA TTA GCT GCT
    met arg phe pro ser ile phe thr ala val leu phe ala ala ser ser ala leu ala ala
    1                                 10                                           20

CCA GTC AAC ACT ACA ACA GAA GAT GAA ACG GCA CAA ATT CCG GCT GAA GCT GTC ATC GGT TAC
pro val asn thr thr thr glu asp glu thr ala gln ile pro ala glu ala val ile gly tyr
                        150  30                                                     40

TCA GAT TTA GAA GGG GAT TTC GAT GTT GCT GTT TTG CCA TTT TCC AAC AGC ACA AAT AAC GGG
ser asp leu glu gly asp phe asp val ala val leu pro phe ser asn ser thr asn asn gly
                        200  50                                                     60

HindIII  270
TTA TTT ATA AAT ACT ACT ATT GCC AGC ATT GCT GCT AAA GAA GAA GGG GTA TCT TTG GAT
leu phe ile asn thr thr ile ala ser ile ala ala lys glu glu gly val ser leu asp
250                               70                          80              300

HindIII
AAA AGA GAG       GCT GAA GCT TGG CAT TGG CTA GAA GTA AAA CCT GGC CAA ATG TAC
lys arg glu       ala glu ala trp his trp leu gln val lys pro gly gln pro met tyr
                       260      90                          290                102
....... SPACER 1                                                α FACTOR 1

HindIII
AAG AGA GAA GCC GAA GCT TGG CAT TGG CTG CAA CTA AAG CCT GGC CAA ATG TAC
lys arg glu ala glu ala trp his trp leu gln leu lys pro gly gln pro met tyr
310     320                 90                                              123
....... SPACER 2                                                α FACTOR 2
```

FIG.—1A

```
370                  380    HindIII 390              400               420              430
AAA AGA GAA GCC GAC GCT GAA GCT TGG CAT TGG CTG CAA CTA AAG CCC GGC CAA CCA ATG TAC
lys arg glu ala asp ala glu ala trp his trp leu gln leu lys pro gly gln pro met tyr
                                                                                    144
      SPACER 3                            αFACTOR 3
            440            450   HindIII 460              470        480              490
AAA AGA GAA GCC GAC GCT GAA GCT TGG CAT TGG TTG CAG TTA AAA CCC GGC CAA CCA ATG TAC
lys arg glu ala asp ala glu ala trp his trp leu gln leu lys pro gly gln pro met tyr
                                                                                    165
      SPACER 4                            αFACTOR 4
          500       510       520    SalI
TAA GCCCGACTGATAACAACAGTGTAGATGTAACAAGTCGACTTTGTTCCCACTGTACTTTTAGCTCGTACAAAATACAAT
stop ATACTTTTCATTTCTCCGTAAACAACCTGTTTTCCCATGTAATATCCTTTTCTATTTTCGTTTCGTTACCAACTTTACACAT

ACTTTATATAGCTAT
```

FIG.—IB

FIG.—2

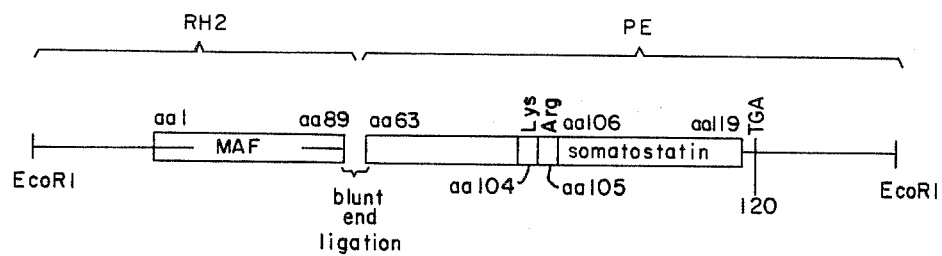
FIG.—3
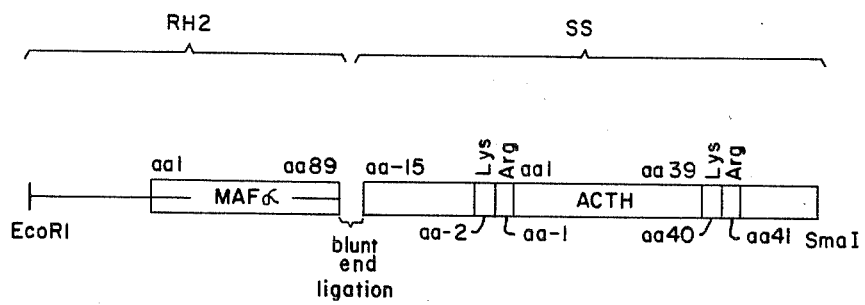
FIG.—4
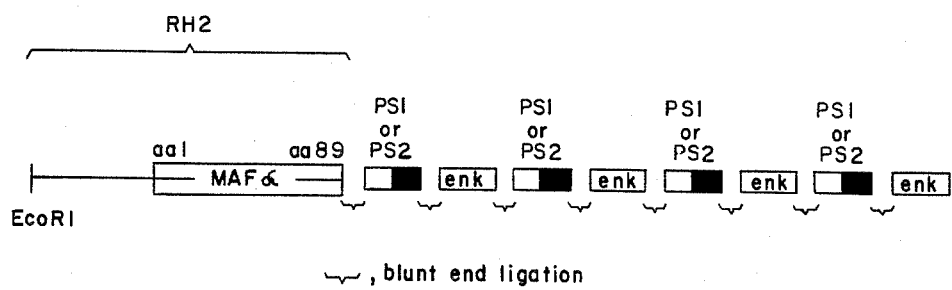
FIG.—5

E. COLI/SACCHAROMYCES CEREVISIAE PLASMID CLONING VECTOR CONTAINING THE ALPHA-FACTOR GENE FOR SECRETION AND PROCESSING OF HYBRID PROTEINS

This invention was made on the Government support under Grant No. AI 18738 awarded by the Department of Health and Human Services. The Government has certain rights in this invention.

This invention relates to the use of recombinant DNA technology to produce biologically useful polypeptides in yeast, and particularly to vectors including the gene coding for *Saccharomyces cerevisiae* alpha-factor useful for production of such polypeptides.

With the onset of recombinant DNA technology, often referred to as the field of genetic engineering, it has become possible to make recombinant DNA molecules which may be expressed in particular microorganisms. It has been possible for example to modify bacteria and yeast to produce various heterologous polypeptides, i.e., polypeptides which would not be normally produced in the host microorganism.

A primary tool of genetic engineering is a structure called a plasmid. A plasmid is usually a circular bit of nonchromosomal autonomously-replicating DNA. It has been found that insertions and rearrangements of genes within the plasmid are consistent with continued replication and growth of the host organism. Included in the information encoded in plasmid DNA is that required to reproduce the plasmid in daughter cells (i.e., an origin of replication) and ordinarily one or more characteristics which permit clones of the host cell containing the plasmid to be selectively grown.

Another key tool of genetic engineering is a process known as transformation. By this process one can induce genetic modification of an organism, heretofore usually a bacterium such as *E. coli*, by incorporating therein fragments of DNA from other sources, such as a plasmid. The procedure for transformation of yeast is described by Hinnen et al., *Proc. Natl. Acad. Sci. U.S.A.*, 75:1929 (1978) and by Beggs, *Nature*, 275:104 (1978).

By a process known as selection, clones of the host cell resulting from transformation which contain the plasmid may be selectively grown. If the transformation is to be performed by host bacteria, a plasmid may be chosen which contains a gene for resistance to an antibiotic. If the transformation is to be performed in yeast, a plasmid may be chosen which contains a gene conferring the ability of cells to grow in the absence of a required nutrient, such as, a particular amino acid. Therefore, depending on the selection trait of the plasmid, only clones containing the plasmid will grow in cultures containing the antibiotic or in cultures without the required nutrient.

The utility of plasmids lies in the fact that they can be specifically cleaved by one or another restriction endonucleases (also known as restriction enzymes) each of which recognizes a particular sequence of nucleotides and cleaves them in a particular way. See R. B. Wickner, *Methods of Molecular Biology*, Vol. 9 (Marcel Dekker, Inc., New York); Mertz et al., *Proc. Natl. Acad. Sci. U.S.A.*, 69, 3370 (1972). Usually the cleavage of double stranded DNA by a particular restriction enzyme results in two so-called sticky ends at which the two DNA strands are of unequal length by one to four nucleotides. These ends can only be joined (ligated) to complementary sticky ends which have been cleaved by the same restriction enzyme. The enzymes which join ends of fragment DNA are known as ligases. If one needs to join a sticky end to another, non-complementary fragment, then the sticky ends are usually enzymatically filled in to make the DNA strands of equal length (blunting). See Hanningson, *Proc. Natl. Acad. Sci. U.S.A.*, 65, 268 (1970). The same ligating enzyme used in higher concentration will join blunted fragments (see Sgaramella et al., *J. Mol. Biol.*, 72, 427–44 (1972)). The theory of genetic engineering therefore is to begin with a plasmid wherein the relative locations of various genes, including genes for selectable characteristics, are known along with the various locations of particular restriction sites (which are cleavable by particular enzymes) and to cleave the plasmid with restriction enzymes. Thereafter heterologous genes or gene fragments may be inserted into the plasmids at a cleavage site. The recombinant plasmid may be introduced into an organism by transformation. By various selection and purification processes the desired transformant may be isolated and grown and which thereby produces a desired heterologous polypeptide.

In yeast the location of the translational start and translational stop signal on mRNA derived from a recombinant plasmid is especially important since if they are not precisely placed to bracket the desired structural gene, a fusion protein will result which may include only part of the amino acid sequence of the desired end product as well as one or more additional lengths of superfluous protein.

A further problem which may occur with use of bacteria derived plasmids to produce mammalian proteins on an industrial scale is that bacteria do not utilize the protein secretion and protein processing mechanisms found in eukaryotes. Therefore, while bacteria may be used to make mammalian proteins, the presence of heterologous proteins in the bacterial cell may have an adverse effect on cell metabolism. However, since yeast is known to have protein secretion and protein processing mechanisms similar to those in other eukaryotes, it may be possible for the yeast cells to remain healthy during production of the heterologous proteins. There has, however, heretofore not been a method by which one could assure the secretion of a heterologous peptide from yeast cells.

It is therefore an object of the present invention to provide a method for causing heterologous polypeptides expressed in yeast from recombinant DNA to be secreted from the yeast cells.

It is a further object of the present invention to provide a method for expression of useful heterologous polypeptides in yeast which do not contain fused superfluous amino acid sequences.

The following is a brief description of the drawings.

FIGS. 1A and 1B are the coding sequence for alpha factor precursor and the amino acid sequence of expressed alpha factor precursor.

FIG. 2 is a partial schematic of the alpha-factor precursor illustrating the relationship of the spacer and alpha factor segments.

FIG. 3 is an illustration of the approach described in Example 9a for fusion of a segment of the precursor for somatostatin to an amino-terminal segment of alpha-factor gene.

FIG. 4 is an illustration of the approved described in Example 96 for fusion of the corticotropin (ACTH) gene to an amino terminal segment of the alpha-factor precursor gene.

FIG. 5 is an illustration of the approach described in Example 9c for construction of a hybrid alpha-factor precursor-enkaphalin polypeptide.

The present invention provides a method for cloning the gene for the polypeptide alpha-factor, which is a secreted polypeptide in the yeast Saccharomyces cerevisiae. The alpha-factor is a polypeptide composed of twelve and thirteen amino acids which is secreted by S. cerevisiae cells of the alpha mating type, but not by cells of the a or a/alpha types. The fusion by known methods of the alpha-factor gene to genes of other useful proteins such as the genes for interferon, hepatitis coat protein, etc., may cause the expression of a fused protein and secretion thereof from the yeast cell into the growth medium. In addition, these fusions may result in the production of interferon, hepatitis coat protein, etc. that lack superfluous amino acids.

According to the present invention it has been found that the alpha-factor precursor gene comprises a plurality of sequences coding for alpha-factor, particularly four, separated from one another by spacer nucleotide regions. It has been found that these spacer regions provide peptides which are substrates for the yeast proteolytic processing system. Thus, by deleting the alpha-factor coding sequences in the alpha-factor precursor and by inserting other useful proteins between the spacer coding regions, or by fusing to these regions, the resultant fusion polypeptide is not only be expressed, but also may be secreted from the yeast cell and processed by the yeast proteolytic processing enzymes to yield multiple copies of the desired protein.

Mating in yeast appears to be facilitated by oligopeptide pheromones ("mating factors") that cause arrest of cells of opposite mating type in the G1 phase of the cell division cycle. Yeast alpha cells produce the alpha-factor, which has two forms, 13 and 12 L-amino acids in length, the latter lacking the N-terminal Trp residue of the tridecapeptide. Yeast a cells produce a-factor, which is 11 L-amino acids in length and has two forms that differ in the sixth residue (Leu or Val). Synthesis of alpha-factor requires cellular RNA and protein synthesis (Scherer et al., *J. Bacteriol.* 119:386 (1974)). Based on these observations and by analogy with mammalian peptide hormones, there is support for the proposal that the yeast mating factors are derived by proteolytic processing from a larger precursor. We have thus cloned the alpha-factor structural gene (MAF alpha, "alpha mating factor") and determined the structure of the precursor.

The alpha-factor precursor gene was cloned as follows. A clone bank in plasmid YEp13 carrying random segments of yeast DNA was transformed into a mat alpha-2 strain and screened for colonies able to secrete alpha-factor by halo formation on a lawn of a cells. One such plasmid with a 4 kb insert (plasmid MAF alpha) was obtained. The gene responsible for halo formation is on 1.7 kb EcoRI fragment and is inactivated by cleavage with HindIII. Sequencing adjacent to the HindIII site showed a nucleotide sequence of approximately 800 base pairs as shown in FIG. 1. The 165 amino acid peptide produced from the translation of nucleotide positions 1–495 in FIG. 1 is the alpha-factor precursor.

The first 20 to 22 amino acids of the alpha-factor precursor comprise a polypeptide segment that is structurally similar to amino terminal segments of other proteins from bacteria and mammalian cells which are secreted from the cells. Therefore, this 20 to 22 amino acid region is called the signal peptide which provides the information which directs the alpha-factor precursor and ultimately then the mature alpha-factor to be secreted. The first half of the precursor also contains three potential sites for glycosylation (asn-X-thr), at positions 23–25, 57–59 and 67–69, which may also be essential for secretion.

The mature form of the alpha-factor is thirteen amino acids long and it may be seen from FIG. 1 that the precursor codes for four tandemly arranged copies of the mature alpha-factor. The sequence from nucleotide 250–495 is schematically shown in FIG. 2, wherein the four alpha-factor genes are alpha F1, alpha F2, alpha F3 and alpha F4 and the spacer sequences are S1, S2, S3 and S4. The four alpha factors have the same amino acid sequence but the corresponding nucleotide sequences differ by a total of 7 nucleotides. The nucleotide sequences of S3 and S4 are identical and they code for Lys-Arg-Glu-Ala-Asp-Ala-Glu-Ala. In S2, Glu replaces Asp and S1 is shorter than the other spacer sequences by two amino acids. Therefore, because the mature form of the alpha-factor is thirteen amino acids in length, the precursor must be processed by proteolytic activities present in yeast cells which cleave the mature alpha-factors from the spacers. These spacer peptides are presumed to contain the recognition regions which determine how the precursor is proteolytically processed. The end of the precursor occurs immediately after the final alpha-factor coding sequence so the processing of the precursor and secretion of the alpha-factor does not appear to require the presence of any amino acids on the carboxy- terminal end of the precursor peptide.

We have found that the plasmid MAF alpha carrying the alpha-factor gene does not secrete alpha-factor when the plasmid is present in a cells, and produces only low levels when present in yeast mutants that are defective in the MAF alpha-1 gene. Also we observe that yeast strains carrying a wild type MAF alpha gene overproduce alpha-factor, i.e., they secrete more alpha-factor than do MAT alpha strains which do not carry the MAF alpha plasmid.

The nucleotide sequence shown in FIG. 1 identifies several sites for recognition by restriction endonucleases. These are particularly, a PstI site at positions 23–28, a TaqI site at position 143–146, and HindIII site at positions 263–268, 326–331, 389–394, and 452–457. By use of conventional restriction endonuclease methods other coding information may be readily fused to the signal peptide or to other regions of the alpha-factor gene. For example, fusion of the coding information for interferon, hepatitis protein or other protein to the amino terminal segment of the alpha-factor gene may result in the secretion of a fused protein from the yeast cell into the growth medium.

Furthermore, derivatives of the alpha-factor precursor gene (MAF alpha gene) may be constructed wherein the alpha-factor coding sequences are deleted but which maintain the spacer peptides and their associated HindIII sites. The insertion of other coding sequences between the spacer peptides by conventional methods will result in the production of a protein containing multiple copies of the inserted coding sequence. Such a modified precursor peptide will not only be secreted, but, because of the presence of the spacer peptide sequences, will also be processed by the yeast proteolytic processing enzymes to yield multiple copies of the mature, native polypeptide.

It will be readily apparent to those of ordinary skill in the art that many conventional modifications may be made of the alpha-factor to utilize its characteristics of causing protein secretion and yeast proteolytic processing. For example, since the production of alpha-factor from the MAF alpha plasmid requires a functional MAT alpha-1 gene, a plasmid constructed of MAF alpha and a yeast mutant which produces a temperature-sensitive MAT alpha-1 protein (P. J. Kushner et al., *Proc. Nat. Acad. Sci., U.S.A.*, 76; 5264–5268 (1979)), which is a strain having functional alpha-1 activity at room temperature (25° C.) and non-functional alpha-1 activity at 34° C., is one in which the production of hybrid proteins may be controlled by controlling the growth temperature of the culture.

The alpha factor gene may also be put under other types of control, such as by fusion to a yeast GAL gene which may lead to an alpha factor gene which is activated by the sugar galactose.

By fusion of coding information for polypeptides of commercial importance to the alpha-factor gene, a high number of copies of the polypeptides may be produced in yeast and secreted from the yeast cells and easily isolated for further purification. The supernatant fluid from the culture medium, for example, may be collected by filtration to separate the fluid from the cell matter and the polypeptide may be isolated from the culture filtrate. Because only a small fraction of all proteins produced by yeast cells is secreted, the culture filtrate will be greatly enriched in the polypeptide of interest. Isolation of the polypeptide of interest from the culture fluid therefore represents a great initial purification of this material in comparison with previous methods in which the material of interest is not secreted, in which case it must be purified away from the many proteins of the yeast cells.

A fused protein produced by yeast cells will have to be proteolytically processed as a part of the industrial preparation of the polypeptide, to separate the alpha-factor segment from the polypeptide of interest. Some of the proteolytic processing, however, may be accomplished by the yeast cells themselves, which would result in a secretion of the mature polypeptide of interest. For example, fusion of the coding sequence for the polypeptide of interest to the HindIII site at positions 263-268 leaves intact the first spacer peptide which may be the recognition signal for proteolytic processing by yeast enzymes. In such a case the yeast cell may secrete the mature form of the polypeptide of interest, thereby obviating the necessity of processing a fusion product as part of the industrial preparation of the polypeptide. In any event, another important advantage of the present invention is that the secreted polypeptide, whether in mature form or as a fusion product, will be outside of the cell and not subject to proteolytic activity capable of destroying the polypeptide within the yeast cell. Therefore another advantage of secretion of the polypeptides or fusion product from the yeast cell is to result in stabilization of the polypeptide.

As described hereinabove, by deletion of the coding sequences of the alpha-factors from the precursor gene and insertion of the coding sequences of heterologous polypeptides, a precursor peptide may be produced containing multiple copies of the heterologous polypeptide flanked by spacer peptides. Since the spacer peptides may provide the proper signals for proteolytic processing by the yeast proteolytic system, such a genetic construction may result in secretion of multiple copies of the mature polypeptide from the yeast cells. Therefore, strains carrying multiple copies of the heterologous polypeptide would exhibit great overproduction of the desired peptide.

Furthermore, by constructing coding sequences using the spacer sequences, the spacers may be placed in sequences for larger polypeptides to provide processing sites which are valuable in several ways. For example, a modified insulin gene may be constructed wherein the sequences that code for the a and b chains of insulin are separated by the sequence coding for the spacer peptide. Such a spacer-insulin hybrid protein would be processed into a and b fragments by the yeast processing enzymes. Another use of the spacer sequence would be to insert the spacer sequence before a polypeptide, such as somatostatin, to form a structure as follows: alpha-factor precursor (residues 1–83)—spacer 1—somatostatin. Processing of this hybrid precursor by the alpha-factor processing system would yield somatostatin with no additional amino acid residues at its amino terminus. This use of the alpha-factor spacer would allow production of somatostatin in yeast which is identical to natural somatostatin.

The present invention is more fully described by, but not limited to, the following examples.

EXAMPLE 1

Isolation of Plasmid p69A which allows Production of Alpha-Factor by mat alpha-2 Mutants We have used a clone bank as described in Nasmyth et al., *Proc. Nat. Acad. Sci. U.S.A.*, 77: 2119 (1980), that contains random genomic fragments of yeast DNA inserted into high copy number plasmid YEp13. This plasmid contains the origin of replication of the yeast 2u plasmid and is present in 30–50 copies per yeast cell (See Broach et al., *Cell* 21:501 (1980)). A mat alpha-2 leu2 recipient (strain XK41-10b) was transformed with plasmid DNA isolated from the clone bank, and 17,000 Leu+ transformants were selected, pooled, and replated on selective medium (lacking leucine). Approximately 50,000 colonies were screened for production of alpha-factor by the halo method. One colony (K69) was found that exhibited a small, distinct halo on lawns of *a* tester cells. To confirm that the halo resulted from production of alpha-factor and not, for example, from production of killer toxin, which also forms a halo on sensitive hosts, we assayed K69 for alpha-factor by the confrontation assay described below. K69 secreted a factor that elicited cell cycle arrest and aberrant cell morphology in *a* cells, indicating that it produces alpha-factor. Production of alpha-factor by K69 requires presence of a plasmid (p69A) in these cells: colonies grown nonselectively (in the presence of leucine) that lose the Leu+ plasmid also lose halo-forming ability. Plasmid p69A thus appears to contain a determinant that allows the mat alpha-2 recipient to produce alpha-factor.

EXAMPLE 2

Behavior of Plasmid p69A in Different Strains

Plasmid p69A was introduced into various yeast strains differing in their mating type locus and in the BAR1 gene to determine whether it affected alpha-factor synthesis. These results are shown in Table 1.

Alpha-factor was assayed by halo formation on lawns of the most sensitive *a* tester strain (RC631), which carries the sst2-1 mutation. As expected, re-introduction of p69A into a mat alpha 2-4 strain yielded cells that produced alpha-factor. This strain is still defective in mating; hence, p69A does not contain a functional MAT alpha-2 gene. However, MAT alpha strains carrying p69A produced a considerably larger halo than did MAT alpha strains carrying YEp13. A further indication that p69A leads to overproduction of alpha-factor is that wild type MAT alpha strains carrying p69A form a halo on MATA SST2+ lawns. Plasmid p69A thus contains a gene whose expression is limiting for alpha-factor production in a wildtype alpha cells as well as in mat alpha-2 mutants. The observation that (p69A)/mat alpha 1-5 strains produce very little alpha-factor is not unexpected since alpha 1 product is necessary for alpha-factor synthesis.

TABLE 1

Production of alpha-factor by strains carrying plasmid p69A.

| Plasmid | Nuclear Genotype | alpha-factor production assayed on tester lawns | |
|---|---|---|---|
| | | MATa sst2-1 | MATa SST2 |
| p69A | mat alpha 2-4 | + | — |
| p69A | MAT alpha | +++ | + |
| p69A | mat alpha 1-5 | +/— | — |
| YEp13 | MAT alpha | ++ | — |
| p69A | MATa bar1-1 | +/—[a] | — |
| p69A | MATa BAR1[b] | — | — |

Legend to Table 1

Strains carrying various plasmids were tested for alpha-factor production by the halo assay at 30° on BBSD medium (to select for maintenance of the plasmid) as described below. MATa testers were strains 227 (SST2) and RC231 (sst2-1). ++, wildtype alpha-factor halo; +, halo smaller than wildtype; +++, halo larger than wildtype; +/—, small halo; —, no halo. [a]Halo size varies in different segregants from no halo to a halo as large as by (p69A/mat alpha 1-5 strains. [b]This (p69A)/MATa strain did not show an increased level of a-factor. mat alpha 2-4, mat alpha 1-5, and MATa strains carrying YEp13 did not produce alpha-factor.

EXAMPLE 3

Sequencing of Plasmid p69A

Prior to sequencing, the determinant for alpha-factor synthesis was localized within the 4 kbp insert present in plasmid p69A. The insert contains three EcoRI sites, which define segments R1-1, R1-2, R1-3 and R1-4. The R1-2 fragment contains a cluster of four HindIII sites (see FIG. 1) which are separated from each other by 63 bp. Plasmids lacking different EcorRI fragments were constructed by partial digestion with EcoRI followed by religation and were tested for alpha-factor production in XK41-10b. These results indicate that the alpha-factor determinant is located in the 1.7 kbp fragment R1-2: all plasmids containing R1-2 allow alpha-factor production, whereas all plasmids lacking this fragment do not (see Table 2 below). Plasmids that carry either the region of R1-2 to the left of the HindIII site cluster (YEp13-H2) or to the right of the cluster (YEp13-H1) do not produce alpha-factor. These results indicate that the HindIII sites of R1-2 lie within the gene responsible for alpha-factor production.

The sequencing strategy of fragment R1-2 is as follows. See FIG. 2. First, HindIII sites 1 (position 268) and 4 (position 457) were 3' end-labelled, and the sequences to the right of site 4 (and to the left of site 1) were determined. The last T of HindIII site 4 (position 457) is the start of a sequence that codes for the alpha-factor tridecapeptide, which is followed immediately by a TAA translational termination signal. Sequencing leftwards from a SalI site forty basepairs downstream of the alpha-factor coding sequence revealed the presence of four tandem sequences coding for alpha-factor. Each of these sequences is preceded by a similar coding sequence of 18 or 24 nucleotide pairs. Further sequence determination reveals an ATG located 89 amino acids upstream from the first alpha-factor sequence. We have sequenced both DNA strands between the HinfI site 1 and SalI, which includes the entire coding region and some flanking regions. The remainder of the sequence has been determined for only a single DNA strand. The sequence is shown in FIG. 1.

Nucleotide sequence analysis thus revels that plasmid p69A contains sequences coding for alpha-factor that are contained within a large coding sequence, an alpha-factor precursor. The key features of this sequence are: (1) The precursor is 165 amino acids long, beginning with ATG and ending at TAA immediately following alpha-factor sequence 4. (2) The precursor contains four sequences coding for identical alpha-factor tridecapeptides (alpha-factor 1, 2, 3, 4). (3) Between these alpha-factor sequences are regions coding for similar octapeptides, which we refer to as peptide "spacer" S2, S3, and S4. Preceding alpha-factor 1 is a similar amino acid sequence of six amino acids (spacer 1, S1).

TABLE 2

Localization of the alpha-factor determinant in p69A

| YEp13 derivative containing fragments | alpha-factor production by mat 2-4 strain carrying plasmid |
|---|---|
| R1-1, R1-2, R1-3, R1-4 | + |
| R1-4 | — |
| R1-1, R1-4 | — |
| R1-3, R1-4 | — |
| R1-1, R1-3, R1-4 | — |
| R1-1, R1-2, R1-4 | + |
| R1-2, R1-3, R1-4 | + |
| H1 | — |
| H2 | — |
| none | — |

Legend to Table 2

The plasmid carrying fragment H1 contains the H1 HindIII fragment from p69A inserted into YEp13. All other plasmids are deletion derivatives of p69A. Plasmids were introduced into mat alpha 2-4 strain XK41-10b and tested for alpha-factor production as described below.

EXAMPLE 4

Strains and Plasmids

Strains are given in Table 3. The yeast clone bank was constructed in vector YEp13 by insertion of yeast genomic DNA fragments partially digested by endonuclease Sau3a. YEp13 is a derivative of pBR322 containing the yeast LEU2 gene and a yeast origin of replication from the 2u plasmid (Broach et al., Gene 8:121 (1979)). Plasmid pBR322-MAT alpha (containing the EcoRI fragment of MAT alpha) as described by Nasmyth and Tatchell Cell 19: 753-764 (1980). YEp13-MAT alpha, which contains a HindIII subfragment from pBR322-MAT alpha, was also constructed.

TABLE 3
Strain List

| Strain | Relevant Genotype | |
|---|---|---|
| DC5 | MATa leu2-3 leu2-112 his3 can1 | (Broach et al, Gene 8:12 (1979)) |
| DC6 | MAT leu2-3 leu2-112 | |
| G121c3-24a | his4 can1 mat 2-4 cry1 | |
| XK41-10b | leu2 his4 mat 2-4 cry1 HMLa leu2-3 leu2-112 | (segregant from DC5 X G121C3-24a) |
| RC629 | MATa sst1-2 rme ade2-1 his6 | (Chan et al., Molec. Cell Biol. 2:11 (1982)) |
| RC631 | MATa sst2-1 rme ade2-1 | (Chan et al., supra) |
| AB320 | his6 HO ade2-1 lys2-1 trp5-2 leu1-12 | (Nasmyth et al., Proc. Nat. Acad. Sci. U.S.A., 77:2119 (1980)) |
| G116-4A | mat 1-5 cry1 ura3 trp1 his4 leu2 | |
| XK96A2-6b | mat 1-5 cry1 leu2-3 leu2-112 trp1 | (segregant from G116-4A X DC5) |
| G245-24C | MATa bar1-1 leu2-3 leu2-112 trp1 | |
| 227 | MATa lys1 cry1 | |

Media

E. coli were grown on LB agar supplemented as necessary with ampicillin (100 ug/ml) or tetracycline (20 ug/ml). Yeast complete medium (YEPD) and synthetic minimal medium (SD) are described in Hicks et al., Genetics 83:245 (1976). Alpha-factor halo assays were performed on YEPD and SD media (BBMB and BBSD, respectively), buffered as described by Fink et al. Proc. Nat. Acad. Sci., U.S.A., 69:2846 (1972).

Enzymes and Radiochemicals

Restriction endonucleases were obtained as follows: Fnu4H (gift from D. Russell and M. Smith), EcoRI (Miles Laboratories), and other enzymes from New England Biolabs. DNA ligase was obtained from P-L Biochemicals, calf alkaline phosphatase (grade I) and E. coli DNA polymerase I (Enzym A n. Klenow) from Boehringer Mannheim. alpha$^{32}$P-dATP, used for end-labelling of DNA fragments, were obtained from Amersham (2000-3000 ci/mmol) or from New England Nuclear (600 Ci/mmol or 2000-3000 Ci/mmol).

EXAMPLE 5

Assays

Alpha-factor Assays: Production of alpha-factor by colonies or patches of cells was assayed on agar medium by the halo method (modified from Fink et al., supra) or on thin agar slabs by the confrontation assay (Duntze et al. Science 168: 1472 (1970)). Halo assay: Approximately 10$^7$ a cells were spread on BBMB or BBSD plates and were imprinted by replica plating with colonies or patches of cells to be tested for alpha-factor production. In most assays, the a tester was strain RC631, which carries the sst2-1 mutation (Chan et al., supra). Under these conditions, mat alpha 1-5 and mat alpha 2-4 mutants produce a halo at room temperature but not at 30° or 34°.

Confrontation assay: A line of cells (approximately 10$^5$-10$^6$) to be tested for alpha-factor production was streaked on a thin agar slab (either YEPD or minimal medium). Individual a cells (usually MATa sst1-2 strain RC629) were then placed near the line of cells by micromanipulation and observed for response to alpha-factor (inhibition of budding, formation of elongated cells). Transformants carrying YEp13-derived plasmids were tested on minimal medium lacking leucine (to select for the plasmid) and were incubated overnight at 30° before introducing the a tester cells.

EXAMPLE 6

Screening Procedures For Identification of Plasmids Carrying the MAF Alpha Gene Plasmid DNA was extracted from the E. coli-yeast pool and used to transform leu2 mat alpha-2 strain XK41-10b to Leu$^-$ by selection on minimal medium. These colonies were collected and replated on selective medium and then assayed at 30° for production of alpha-factor by the halo assay. Optimal conditions for this assay were developed by monitoring halo formation by colonies of strain XK41-10b carrying plasmid YEp13-MAT alpha. Maximal halo size was obtained under the following conditions: (a) alpha-factor assays were performed on minimal medium to select for maintenance of YEp13. (2) The tester strains used for the alpha-factor halo assay carried a mutation in the SST2 gene, which leads to supersensitivity to alpha-factor (Chan et al., supra).

EXAMPLE 7

Construction of Plasmid Derivatives

The HindIII fragment containing the MAT alpha locus was transferred from pBR322-MAT alpha to YEp13 by cleavage of pBR322-MAT alpha with Hin dIII and ligating to HindIII-cleaved YEp13 which had been treated with calf alkaline phosphatase. YEp13 carrying the 1.3 kbp HindIII fragment of p69A (plasmid YEp13-H2) was constructed in a similar manner. A derivative of p69A lacking the H1 fragment (plasmid YEp13-H1) was obtained by cleavage of p69A with HindIII followed by circularization. Derivatives of p69A lacking different EcoRI fragments were constructed by partial digestion of p69A with EcoRI followed by ligation. Amp$^R$ E. coli transformants that complement the bacterial leuB mutation must contain the 4.6 kb, 4.0 kb and 2.3 kb EcoRI fragments (which includes a small fragment of the yeast insert in p69A (fragment R1-4)). Presence of additional EcoRI fragments (R1-1, 1.1 kb; R1-2, 1.7 kb; R1-3, 1.0 kb) was determined by restriction endonuclease digests. Plasmids were then transformed into the mat alpha 2-4 strain and tested for their ability to produce alpha-factor.

EXAMPLE 8

DNA Sequencing and Hybridization

The sequencing procedure of Maxam and Gilbert (Proc. Nat. Acad. Sci. U.S.A., 24:560 (1977); Methods in Enzymol 65:499 (1980)) was used. DNA fragments were labelled by the 3' end labelling technique (Smith et al., Cell 16:753 (1979)). All restriction endonuclease sites used for labelling DNA ends have been read across in an independent sequence analysis. Hybridizations to restriction endonuclease fragments were performed by the method of Southern (J. Mol. Biol. 98:503 (1975)).

EXAMPLE 9a

Fusion of a Segment of the Precursor For Somatostatin to an Amino-Terminal Segment of the Alpha-Factor Gene The R1-2 fragment of the alpha factor gene is cleaved with HindIII to produce a fragment (denoted RH1). The cohesive end of the HindIII site of this fragment is filled in enzymatically to produce a fragment denoted RH2 to be ligated to a segment of the somatostatin gene. The RH2 fragment is jointed to a PstI-EcoRI fragment (denoted PE) from the sequence that codes for pre-prosomatostatin (which is described in Goodman, R. H., J. W. Jacobs, W. W. Chin, P. K. Lund, P. C. Dee, and J. F. Habener, *Proc. Natl. Acad. Sci., U.S.A.*, 77:5869–5873 (1981). The DNA segment described by Goodman et al. was produced by enzymatic conversion of pre-prosomatostatin mRNA to double-stranded DNA by reverse transcription. Thus the pre-prosomatostatin segment contains no intervening sequences and may be expressed in yeast when fused to yeast expression sequence provided by the MAF alpha gene. The RH2 segment, containing the first part of the alpha-factor gene, is fused with the PE fragment from pre-prosomatostatin by blunt end ligation to yield a structure shown in FIG. 3. This segment is inserted into a high copy number yeast plasmid cloning vector and introduced into yeast by transformation. Since the hybrid alpha factor-somatostatin gene contains the information for secretion of yeast polypeptides (contributed by the alpha-factor segment), the fused protein will be secreted from yeast cells. Alternatively, yeast processing activities that are known to process the alpha factor precursor polypeptide will cleave after the lysine residue (at position 105 in the somatostatin segment) to liberate native somatostatin. No processing at the carboxy terminal end of somatostatin is necessary because the somatostatin coding sequence is followed by a translation termination signal.

EXAMPLE 9b

Fusion of a Segment of the Corticotropin (ACTH) Gene to an Amino Terminal Segment of the Alpha Factor Precursor Gene The RH2 fragment described in Example 9a is joined to a DNA segment containing coding information for ACTH, such as, the sequence coding for bovine pre-pro ACTH. The bovine ACTH precursor segment is described by S. Nakanishi, A. Inoue, T. Kita, M. Nakamura, A. C. Y. Chang, S. N. Cohen, and S. Numa, *Nature* 278: 423–427 (1979). The segment is a double-stranded DNA derivative of the corresponding mRNA and thus does not contain any intervening sequences. This segment contains sites for the restriction endonuclease SmaI which cuts between amino acid residues -16/-15 and between residues 86/87 to yield a DNA segment denoted SS. ACTH (positions 1–39) is located between these SmaI sites. The RH2 fragment from the alpha factor gene is joined by blunt end ligation to the SS fragment containing ACTH (See FIG. 4). This segment is inserted into a high copy number yeast plasmid cloning vector and introduced into yeast by transformation. Rationale: As in Example 9a, a hybrid protein is produced and is secreted from yeast cells. Furthermore, yeast proteolytic processing activities cleave this hybrid precursor molecule at the Lysine and Arginine residues that flank ACTH to liberate native ACTH, which is secreted from yeast cells.

EXAMPLE 9c

Construction of a Hybrid Alpha Factor Precursor-Enkephalin Polypeptide which Produces Secreted and Mature Enkephalins The segment RH2 is described in examples 9a and 9b. A DNA segment (denoted ME) coding for met-enkephalin (Tyr-Gly-Gly-Phe-Met) is synthesized enzymatically according to methods described and utilized by Comb, M., E. Herbert, and R. Crea, *Proc. Natl. Acad. Sci., U.S.A.*, 79:360–364 (1982). DNA segments that code for Lys-Arg and for Lys-Arg-Glu-Ala-Glu-Ala-Glu-Ala are synthesized by analogous methods. These segments provide processing sites (denoted PS1 and PS2, respectively). Met-enkephalin segments are jointed to PS1 or to PS2 segments by blunt end ligation. The (ME, PS1) and (ME, PS2) ligation mixtures are joined to RH2 by blunt end ligation and are inserted into a high copy number yeast plasmid cloning vector (see FIG. 5). The population of resultant plasmids is introduced into yeast cells and assayed for secretion of enkephalins. The yeast alpha-factor segment provides coding signals for secretion of the precursor molecule. The mature enkephalin molecules are cleaved from the hybrid precursor by yeast proteolytic activities that cleave after Lys-Arg or after Lys-Arg-Glu-Ala-Glu-Ala-Glu-Ala. Lys residues are removed from the carboxy terminus of enkephalin by yeast carboxypeptidase.

What is claimed is:

1. A DNA expression vector capable of expressing in yeast cells a product which is secreted from said yeast cells, said vector comprising at least a segment of alpha-factor precursor gene and at least one segment encoding a polypeptide.

2. A DNA expression vector according to claim 1 wherein said segment encoding a polypeptide is an insertion into said alpha-factor precursor gene.

3. A DNA expression vector according to claim 1 wherein said segment encoding a polypeptide is a fusion at a terminus of said alpha-factor precursor gene.

4. A DNA expression vector according to claims 2 or 3 wherein coding sequences for mature alpha-factor are absent from said segment of alpha-factor precursor.

5. A DNA expression vector according to claim 1 wherein said polypeptide is somatostatin.

6. A DNA expression vector according to claim 1 wherein said polypeptide is ACTH.

7. A DNA expression vector according to claim 1 wherein said polypeptide is an enkephalin.

8. A yeast strain transformed with a DNA expression vector of claim 1.

9. A method for producing a DNA expression vector containing alpha-factor gene comprising the steps of
 (a) transforming a MAT alpha2 leu2 yeast strain with a gene bank constructed in plasmid YEp13;
 (b) selecting for Leu+ transformants from the population formed in step (a);
 (c) replating the transformants from step (b) and
 (d) screening for alpha-factor producing colonies.

10. A DNA expression vector formed according to the method of claim 9.

* * * * *